US008403861B2

(12) United States Patent
Williams et al.

(10) Patent No.: US 8,403,861 B2
(45) Date of Patent: Mar. 26, 2013

(54) DETECTION OF RESPIRATORY SYSTEM LESIONS (75) Inventors: Deryk John Peter Williams, Woking (GB); Mark Sinclair Varney, Bishopstoke (GB); Michael Garrett, Woking (GB)

(73) Assignee: Anaxsys Technology Limited, Send (GB)

( * ) Notice: Subject to any disclaimer, the term of this patent is extended or adjusted under 35 U.S.C. 154(b) by 0 days.

(21) Appl. No.: 12/874,456

(22) Filed: Sep. 2, 2010

(65) Prior Publication Data

US 2012/0165693 A1   Jun. 28, 2012

(51) Int. Cl.
*A61B 5/08* (2006.01)
(52) U.S. Cl. .......... 600/532; 600/529; 600/537
(58) Field of Classification Search .......... 600/484, 600/529–543
See application file for complete search history.

(56) References Cited

U.S. PATENT DOCUMENTS

| | | | |
|---|---|---|---|
| 4,795,543 A | 1/1989 | Stetter et al. | |
| 5,131,990 A | 7/1992 | Kulwicki et al. | |
| 5,585,559 A | 12/1996 | Hata | |
| 5,606,264 A | 2/1997 | Licari et al. | |
| 6,014,890 A | 1/2000 | Breen | |
| 6,723,055 B2 * | 4/2004 | Hoffman | 600/538 |
| 6,726,637 B2 * | 4/2004 | Phillips | 600/543 |
| 7,094,206 B2 * | 8/2006 | Hoffman | 600/529 |
| 7,153,272 B2 * | 12/2006 | Talton | 600/543 |
| 7,473,229 B2 * | 1/2009 | Webber | 600/532 |
| 7,914,460 B2 * | 3/2011 | Melker et al. | 600/532 |
| 7,972,277 B2 * | 7/2011 | Oki et al. | 600/532 |

FOREIGN PATENT DOCUMENTS

| | | |
|---|---|---|
| EP | 0 299 780 | 1/1989 |
| WO | 2004/030132 | 4/2004 |
| WO | 2008/009980 | 1/2008 |

OTHER PUBLICATIONS

Baglio, V. et al., "Zeolite-based composite membranes for high temperature direct methanol fuel cells," Journal of Applied Electrochemistry, Feb. 1, 2005, pp. 207-212, vol. 35, No. 2.
Kalkan, A. Kaan et al., "A Rapid-Response, High-Sensitivity Nanophase Humidity Sensor for Respiratory Monitoring," IEEE Electron Device Letters, Aug. 2004, pp. 526-528, Vo. 25, No. 8.
Mortimer, R.J. et al., "AC impedance characteristics of solid-state planar electrochemical carbon monoxide sensors with Nafion as solid polymer electrolyte," Electrochimica ACTA, Aug. 5, 2002, pp. 3383-3387, vol. 47.
Otagawa, Takaaki et al., "Planar Microelectrochemical Carbon Monoxide Sensors," Sensors and Actuators, Jan. 1990, pp. 319-325, vol. 1, No. 1-6.

(Continued)

*Primary Examiner* — Navin Natnithithadha
(74) *Attorney, Agent, or Firm* — McDonnell Boehnen Hulbert & Berghoff LLP (57) ABSTRACT Humidity profiles of exhaled air of individuals obtained using a sensor to detect water vapor content or temperature versus time of exhalation may exhibit an irregularity indicative of a space-occupying respiratory system lesion. Detection of such irregularities provides an inexpensive and rapid means of pre-screening individuals for lung cancer diagnosis, and is applicable even to individuals with other respiratory disorders such as asthma and COPD.

8 Claims, 4 Drawing Sheets

OTHER PUBLICATIONS

Tatara, Tsuneo et al., "An Apnea Monitor Using a Rapid-Response Hygrometer," Journal of Clinical Monitoring, Jan. 1, 1997, pp. 5-9, vol. 13, No. 1.

Tricoli, Vincenzo et al., "Zeolite-Nafion composites as ion conducting membrane materials," Electrochimica ACTA, Aug. 1, 2003, pp. 2625-2633, vol. 48, No. 18.

Van Der Wal, P.D. et al., "Extremely stable Nafion based carbon monoxide sensor," Sensors and Actuators B, Sep. 1996, pp. 119-123, vol. 35, No. 1.

Yasuda, Ayumu et al., "Electrochemical carbon monoxide sensor with a Nafion film," Reactive & Functional Polymers, Jul. 15, 1999, pp. 235-243, vol. 41, Nos. 1-3.

* cited by examiner

DETECTION OF RESPIRATORY SYSTEM LESIONS

FIELD OF THE INVENTION

The present invention relates to determining the presence of space-occupying lesions in the respiratory system of individuals, especially such lesions affecting the lungs or airways, relying on determination of irregularity in the humidity or temperature profile of exhaled breath. Such determination provides a simple, fast means of pre-selecting individuals for diagnosis of respiratory system lesions such as a lung tumour, even at a very early stage of development. While a sensor for this purpose may be a known form of electrochemical sensor as used for determination of respiratory function, e.g. assessing deterioration of respiratory function arising from asthma and/or chronic obstructive lung disease (COPD), also now disclosed are novel sensors for use in predicting the presence of respiratory system lesions as described further herein.

BACKGROUND TO THE INVENTION

The current 5-year survival rate for of lung cancer is 16% in developed countries. In part this is because lung cancer tends to present late and there is no effective early screening programme. There is therefore a need for a low cost, non-invasive, entirely safe screening means for selecting individuals with predicted lung lesions which can be applied by non-specialist staff with the aim of improving early presentation for lung cancer diagnosis and thereby lung cancer survival rates.

In order to have an effective screening programme for lung cancer diagnosis, tumours need to be identified at the T1 (3 cm or less diameter), N0, M0 stage (i.e. before nodal involvement and before the tumour has metastasised). Surgical resection is usually possible at this stage achieving a complete cure.

A fast response ion-exchange humidity sensor that responds in real time to water vapour in a gas stream is disclosed in Published International Application WO 2008/009980 (in common ownership with the present application). The thin layer of ion exchange material extending between the working electrode and the counter electrode of this form of sensor comprises a sulphonated tetrafluoroethylene copolymer (conveniently and preferably Nafion®, available commercially from Du Pont). The humidity profile of serial exhaled breaths can be measured by providing an inlet such that dry gas is directed on to the sensing element during inhalation through the sensor. The sensor is thereby returned to its pre-test state almost instantly. As taught by related published US Application 2008-026370A1, resultant humidograms can be directly correlated with respiratory function and may, for example, be used to assess deterioration of respiratory function associated with respiratory diseases such as asthma.

During the course of preliminary trials of such a device to assess respiratory function, it was surprisingly observed by the inventors that the humidograms occasionally exhibited an irregularity (an indent) in the Phase II initial upward curve portion when compared to the expected profile. Further check on the health of relevant subjects revealed lung cancer.

Most patients with lung cancer come from a population with chronic respiratory symptoms. If smokers were to be referred for imaging every time a new respiratory symptom appears, as some advise, then the healthcare infrastructure would be ill-equipped to cope with demand and this could be seen as an inefficient use of resources. The lack of availability of suitable screening tools to aid decision making on referral for confirmatory lung cancer diagnosis and treatment is thus a constant cause of frustration for oncologists.

There are three leading technologies that are being actively researched as potential screening tools: computed tomography (CT), mass spectrometry and electronic nose technology. CT scanning has been investigated extensively as a potential screening tool. CT scanning presents difficulty in picking up sufficient tumours to justify screening as routine; there is high financial cost and limitations on CT facilities. In addition, the risk of radiation-induced cancers (estimated at 1 fatality per 1300 patients scanned) makes this an unsuitable large scale tool. 'Electronic nose' technology with gas chromatography is a technology that is also being investigated. However, even with highly sensitive machines, no true specificity has been demonstrated and again the high cost of such technology is a problem.

SUMMARY OF THE INVENTION

The inventors have found that a particular type of humidogram profile obtained with an inexpensive, portable electrochemical sensor is an indicator of a lung lesion. This represents an exciting development, especially in relation to lung cancer diagnosis.

In one aspect, there is thus provided a method of pre-selecting an individual for determination of the presence and nature of a space-occupying respiratory system lesion, which may be for example a lung tumour, said method comprising determining whether a humidity or a temperature profile of exhaled air of said individual (generally water vapour content or temperature versus time of exhalation) exhibits an irregularity indicative of such a lesion, said irregularity equating with lowered water vapour content or temperature than to be expected at the same time point after the start of exhalation in the absence of a respiratory system lesion. Thus, where water content or temperature versus time of exhalation is monitored such irregularity will be observed as an indent in the profile compared to the expected profile for a comparable individual without such a lesion.

For this purpose, the individual will exhale breath whereby it impinges on the sensing element of a sensor for sensing water vapour in a gas stream. As indicated above this may be a known form of respiratory sensor as described for example in WO 2008/009980 having a conduit through which the subject can both inhale air drawn in through an inlet and exhale air whereby it is channelled to the sensing element. However, it has been found preferable for breath to be delivered to the humidity sensing element as non-laminar flow equating with a Reynolds number of greater then 2000. This may be achieved by exhalation into a narrow conduit which directs exhaled air to the sensing element, e.g. a conduit selected with bore between 10 and 20 mm, and preferably in the range of 15 to 18 mm, and using a breathing technique to give turbulent flow (for example faster breathing than normal). In this way, humidity changes of interest which develop in the respiratory system are less liable to be lost or reduced.

Tumours smaller than 3 cm in diameter have been shown to be predictable in this way, but other types of lesion may also be detected. By lesion will be understood any space-occupying lesion arising from tissue growth and/or remodelling which affects the respiratory systems, including the lungs and the airways.

Figure 1:
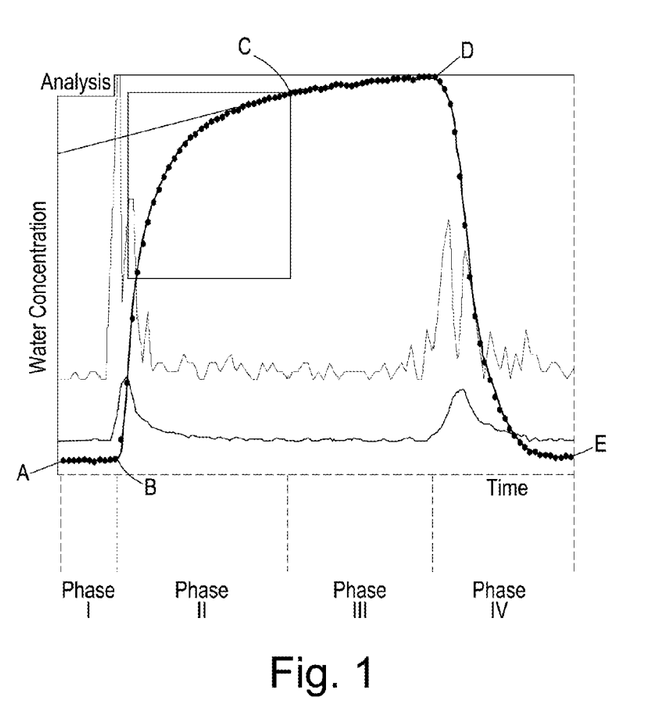
Figure 2:
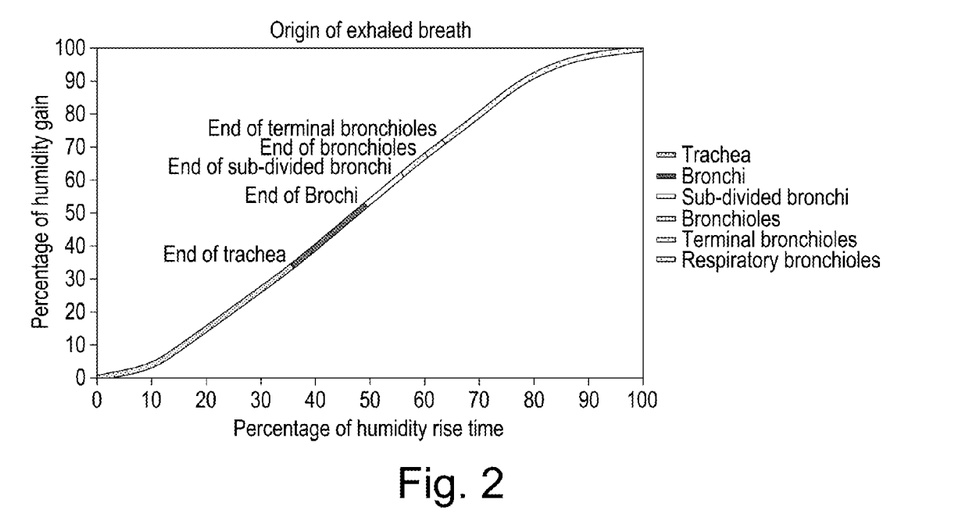

According to a second aspect, there is provided a sensor for sensing water in an exhaled air stream. The sensor is provided with a sensing element disposed to be exposed to the exhaled air stream. The sensing element comprises a working electrode, a counter electrode and a layer of ion exchange material extending between the working electrode and the counter electrode. In use, contact of the ion exchange layer with the air stream forms an electrical circuit between the working and counter electrodes. A conduit is also provided through which the air stream is channelled to impinge upon a sensing element. The conduit is arranged to allow turbulent flow in the air stream, for example by having a diameter in a range of 10 to 20 mm.

According to a third aspect, there is provided a sensor for sensing a temperature of an exhaled air stream. The sensor is provided with a conduit through which the air stream is channelled, the conduit being arranged to allow turbulent flow in the exhaled air, and a temperature sensing element disposed to be able to measure a temperature of the exhaled air in the conduit.

According to a fourth aspect, there is provided a system for pre-selecting an individual for determination of the presence and nature of a space-occupying respiratory system lesion. The system includes a sensor for sensing either water in a stream of exhaled air or a temperature of a stream of exhaled air, means for receiving from the sensor an output from the sensor, and a processor. The processor is used to determine a humidity profile of water vapour content or a temperature profile in the stream of exhaled air, and is also arranged to determine whether the profile exhibits an irregularity indicative of such a lesion. The irregularity equates with lowered water vapour content than would be expected at the same time point after the start of exhalation in the absence of a respiratory system lesion.

BRIEF DESCRIPTION OF THE FIGURES

The invention will be described in more detail below with reference to the following figures.

FIG. 1 is a typical graphical trace of the content of water vapour in the exhaled air stream of human subject having healthy lungs shown against the time of exhalation;

FIG. 2 is a graph of change of water vapour content against time in an exhaled air stream showing the source of exhaled air at different time points after the start of exhalation.

FIG. 3 is a cutaway perspective view of a sensor according to an embodiment of the invention;

FIG. 4 illustrates a system for detecting an irregularity in a humidogram according an embodiment of the invention;

FIG. 5 illustrates a cross-section view of a sensor according to an embodiment of the invention;

FIG. 6 illustrates the effect of turbulent and laminar flow in an exhaled air stream;

FIG. 7 is a graph showing a water vapour content in an exhaled air stream of subject A;

FIG. 8 is a graph showing a water vapour content in an exhaled air stream of subject B;

DETAILED DESCRIPTION

The method of the present invention relies upon detecting the presence of water vapour in an exhaled air stream or the temperature of an exhaled air stream exhaled by a subject. In a preferred embodiment, the method involves determining the change in content of the water vapour in the exhaled air stream over the time of the exhalation. The method may include measuring the actual content of water vapour in the exhaled air stream. However, in general, it is the change in content of water vapour over the time of the exhalation that is more important for the present invention. While the description refers to detecting water content, any derivative of water content such as water concentration, may also be used.

The general profile of the change in content of water vapour over time for a single exhaled breath from a person with healthy lungs is shown in FIG. 1. The profile may be characterised as a curve having various points of inflection indicated as points A, B, C, D and E, which generally separate four phases. Phase I is the volume of gas that is substantially free of water vapour produced by the subject at the very start of exhalation, the gas having the humidity of the atmosphere being breathed by the subject. Phase II is the ascending phase characterised by a rapid increase in the content of water vapour and represents the transition from gas having the background humidity to the gas expelled from the early emptying portions of the lungs of the subject. Phase III is the (alveolar) plateau phase and corresponds to the gas expelled from the later emptying portions of the subject's lungs, during which the content of water vapour in the gas being expelled continues to rise slowly with time. Point D is generally indicated to be the end-tidal content of water vapour. Phase IV of the profile is the final inhalation stage, during which the content of water vapour falls rapidly to that of the ambient gas composition.

As indicated above, it has now been found that deviation from such a profile indicative of lower than expected water vapour content at a given time point (an indent) can be taken as an indicator of presence of a respiratory system lesion. Such deviations will most commonly be observed in Phase II as indicated in FIG. 7.

Determination of such an irregularity in a humidity profile obtained for a test subject may include comparison with a pre-existing profile of another comparable subject apart from absence of a respiratory system lesion. Comparison may be with a control profile from a subject with healthy lungs, but where the test subject has a known respiratory disorder such as asthma or the test subject is a smoker, then comparison may be made with a humidity profile from a control subject who has no respiratory system lesion but shares the same respiratory disorder and/or is also a smoker.

Alternatively or in addition, the method may involve analysing the profile of water vapour content against time of the exhaled gas stream of the subject and generating therefrom a profile consistent with the profile expected from the subject assuming lack of any respiratory system lesion. The actual profile obtained may then be compared with the thus generated profile and deviations between the two identified to provide an indication of the condition of the subject. For example, the actual profile obtained from the subject may be subjected to interpolation between specific points on the profile, so as to generate an expected profile. In particular, the points marking the start of each of the Phases I to IV of the profile may be identified and the profile generated between these points by interpolation. In general, the profile will follow the pattern shown in FIG. 1, allowing the shape of a 'normal' profile to be predicted. In particular, the expected profile will be a generally smooth curve, which may be generated from the actual profile obtained from the subject. A subject with a significant disorder having one or more lesions affecting the lungs will produce a profile that differs from the expected profile generated in this manner, most notably by having one or more discontinuities in the smooth curve of the profile. In particular, as noted above, this deviation may be a lower content of water vapour at a given time than the content indicated by the predicted profile.

In the case that a profile of water vapour content against time corresponding to the expected lung function is generated from the actual profile obtained from the subject, the generated profile may be a complete profile, such as shown in FIG. 1, or a portion thereof. If only a portion of the predicted profile is generated, it preferably includes at least Phase II of the profile, as shown on FIG. 1 and described above.

Where analysis of a humidity profile in accordance with the invention indicates the presence of a lesion, the exhalation time point also provides indication of the position in the respiratory tract. FIG. 2 shows a graph of the change of water vapour content in an exhaled breath against the time of exhalation and identifies the source of gas being exhaled at different time periods during the exhalation cycle.

The method may employ a processor to analyse the profile generated from a given subject and, if appropriate, compare the profile with a profile from a subject known to be healthy or in similar condition and stored within the processor. Alternatively, the processor may analyse the profile obtained from the subject and predict a profile of water vapour content against time corresponding to good health and proper lung function. Thereafter the processor will compare the actual profile obtained with the predicted profile. Suitable processors for carrying out such analysis, generation of predicted profiles and comparison are known in the art and commercially available.

The analysis of the profile of water content against time for the exhaled gas of the subject may encompass the entire profile corresponding to a complete profile as shown in FIG. 1. Alternatively, the analysis of the profile may be limited to one or more portions of the complete profile. In particular, the analysis may be limited to the portion of the profile corresponding to Phase II, either in whole or in part. If only a portion of the profile corresponding to Phase II is analysed for features, it is most preferably the central to later portion that is the portion corresponding to the gas stream exhaled during the middle and later period of time of Phase II.

The method of the present invention may be carried out using the gas stream exhaled by a subject during a single breath. Alternatively, the method may be applied to the subject during tidal breathing, so as to conduct an analysis of the gas stream exhaled during a plurality of breaths. In such a case, the method is seeking to identify features in the profile of one or more breaths that indicate an adverse lung condition. It has been found that at least five consecutive exhalations give good results, as in the early exhalations the individual may not be used to the deep/fast breathing regime, and in later exhalations the individual may start to become tired. By analysing several exhalations, standard deviations of the water content/time for the exhalations may be taken and better results achieved.

The method generally requires the subject to exhale such that at least a portion of the exhaled gas stream enters a suitable apparatus or instrument where the water vapour present in the gas stream may be detected. In one preferred embodiment, the subject is caused to exhale into a suitable conduit of a sensor device, the conduit leading to a sensing element sensitive to water vapour. As indicated above, preferably the conduit enables the subject to both inhale air drawn in through an inlet and exhale air whereby it is channelled to the sensing element. Most preferably, with each inhalation there will be provided a drying air stream to the sensing element whereby humidity changes in serial exhalations may be determined.

As also noted above, it has been found that detection of irregularities of interest may be enhanced by ensuring that exhaled breath is delivered to the humidity sensing element as non-laminar flow equating with a Reynolds number of greater then 2000. This may be achieved by exhalation into a narrow conduit which directs exhaled air to the sensing element, e.g. a conduit selected with bore below 20 mm and for breathing technique to give turbulent flow (faster breathing than normal). In this way, humidity changes of interest which develop in the respiratory system are less liable to be lost or reduced. There are other ways to ensure that turbulent flow is maintained once the air has been exhaled, such as increasing the surface roughness within a conduit of a sensing apparatus, but it is of more importance that the air flow leaving the lungs is turbulent, and so ensuring that an individual uses faster/deeper breathing than usual to ensure turbulence.

As noted above, the method does not provide a diagnosis of the actual condition ailing a subject. Rather, the method provides an indication of likelihood that one or more conditions causing lesions in the respiratory tract may be present. Importantly, the method may be applied to subjects with pre-existing respiratory conditions and still provide a strong indication of the presence of lesions.

Sensing Apparatus

A humidity profile for a method of the invention may be obtained by use of any suitable means for detecting water vapour or analysing the water vapour content of the gas stream being exhaled by the subject. Such means are known in the art and a range of suitable apparatus is available commercially.

A particularly preferred apparatus for analysing the exhaled gas stream is one employing an electrochemical sensor comprising a sensing element for exposing to the gas stream exhaled by the subject comprising a first electrode, a second electrode and an active layer extending between the first and second electrodes to provide an electrical path therebetween, the sensing element being responsive to the content of water vapour in the gas stream exhaled by the subject, whereby the conductivity of the path between the electrodes varies in response to changes in the content of water vapour.

Figure 3:
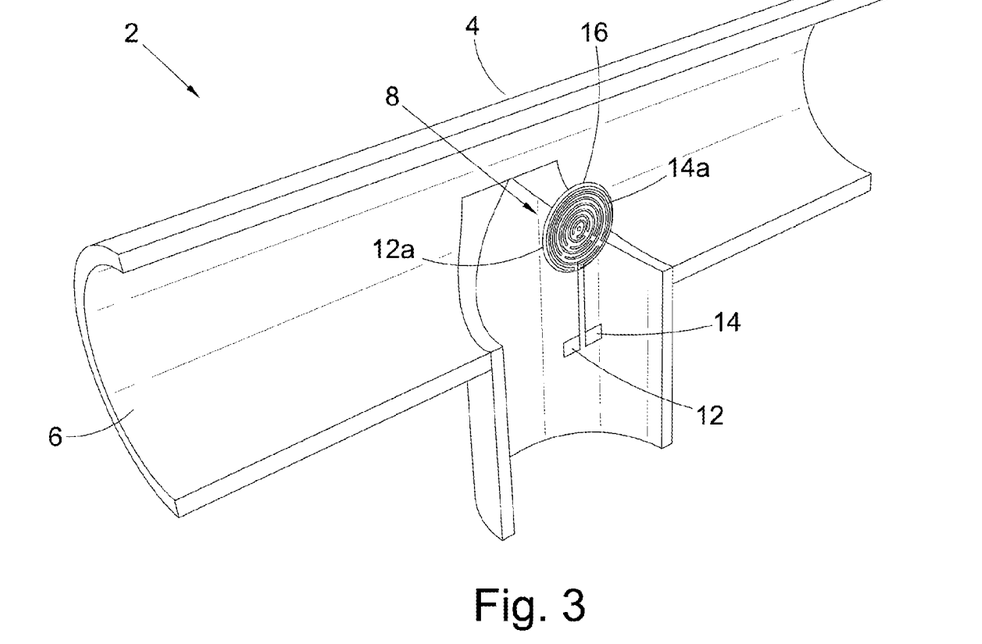

An example sensor is illustrated in FIG. 3. The sensor 2 comprises a conduit 4, through which a stream of exhaled breath may be passed. The conduit 4 comprises a mouthpiece 6, into which the patient may breathe. A sensing element 8 is located within the conduit 4, such that a stream of gas passing through the conduit from the mouthpiece 6 is caused to impinge upon the sensing element 8. The sensing element 8 comprises a support substrate 10 of an inert material, onto which is mounted a working electrode 12 and a reference electrode 14. The working electrode 12 and reference electrode 14 each comprise a plurality of electrode portions, 12a and 14a, arranged in concentric circles, so as to provide an interwoven pattern minimizing the distance between adjacent portions of the working electrode 12 and reference electrode 14. In this way, the current path between the two electrodes is kept to a minimum. It will be appreciated that other arrangements of working electrode and reference electrodes may be used, and the arrangement illustrated in FIG. 3 is by way of example only.

A layer 16 of insulating or dielectric material extends over a portion of both the working and counter electrodes 12 and 14, leaving the portions 12a and 14a of each electrode exposed to be in direct contact with a stream of exhaled air passing through the conduit 4

An ion exchange layer may be conveniently deposited as a coating on top of the electrodes applied to substrate layer.

As indicated above, in one preferred embodiment the sensing element 8 comprises a working electrode 12, a counter electrode 14 and a layer of ion-exchange material extending between said electrodes, the ion-exchange material characterized by comprising a sulphonated tetrafluoroethylene copolymer such as Nafion. In one embodiment, the ion exchange material may also comprise a fine dispersion of a mesoporous material, such as a zeolite. The mesoporous material is preferably dispersed as particles having a particle size in the range 0.5-20 μm, more preferably 1 to 10 μm. The particles of mesoporous material are preferably finely dispersed in the ion exchange layer such that adjacent particles are generally at least one particle diameter apart, more preferably generally at least 3 to 5 particle diameters apart. More highly dispersed arrangements may also be used with particles up to 10 diameters apart. In one specific embodiment of the invention, the ion-exchange layer comprises Nafion having a fine dispersion therein of a zeolite preferably for example, zeolite 4A.

An anti-bacterial filter may be used in the conduit to reduce the risk of cross-contamination between different individuals. The use of two or more filters may be used to increase the back-pressure to exhalation, but this is not thought to assist in the detection of irregularities in the humidity profile.

Such a sensor apparatus may be particularly compact and of very simple construction. In addition, the sensor apparatus may be used at ambient temperature without the need for any heating or cooling, while at the same time producing an accurate measurement of water vapour content in the gas being analysed.

The method requires that an electric potential is applied across the electrodes and conductivity estimated by the measurement of current passing between the electrodes. In one simple configuration, a voltage is applied to the counter electrode, while the working electrode is connected to earth (grounded). In its simplest form, the method applies a single, constant potential difference across the working and counter electrodes. The current that passes between the counter and working electrodes is converted to a voltage using a resistor, R, and recorded as a function of the water vapour content in the gaseous stream.

Figure 4:
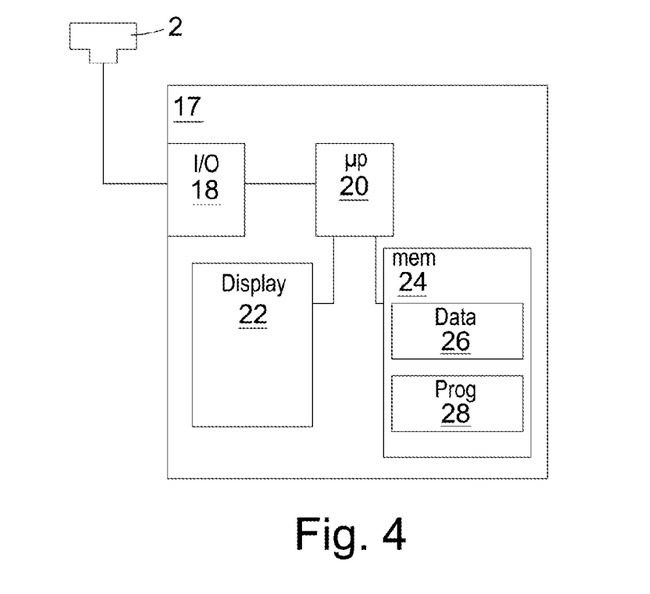

The sensor may be used as part of a system for determining the change in content of the water vapour in the exhaled gas stream over the time of the exhalation, as illustrated in FIG. 4.

The sensor 2 apparatus is operatively connected to a computer device 17 via an in/out device 18. The computer device 17 comprises a processor 20, a display device 22 and a computer readable medium 24 in the form of a memory. The display device 22 can be used for displaying information on the water vapour content in the exhaled gas over the time of one or more breaths. The sensor 2, processor 20 and display 22 may be interconnected by any suitable means and suitable arrangements are known in the art. In one embodiment, the sensor element is wirelessly connected to a suitable signal recording, processing and display system.

The display device 22 may also include means for displaying part or all of an existing profile of a healthy or similar subject and/or a predicted profile generated as described above. Two or more of the aforementioned part or whole profiles may be superimposed on the display to enable a direct visual comparison to be made. It will be appreciated that the display device may display the information in any form suitable for interpretation by an operator. By way of example, while it may display a profile of water concentration against time, as described above, it may display simply an indication of whether or not an irregularity has been detected, or the information in a different graphical format.

The processor 20 may be used for determination of the magnitude of any deviation of the actual profile obtained from the subject with a chosen pre-existing and/or predicted profile. Data relating to the magnitude of the deviation may also be displayed.

In a preferred embodiment, the processor 20 includes means for automated mathematical detection and quantification of irregularities within the humidity profile (water vapour content versus time) of an exhaled breath whereby data is transformed for ease of detection and determination of magnitude of indents. Techniques for such curve analysis are known.

The memory 24 may be used to store data 26. These data may include recorded data for analysis, and pre-recorded data for comparison in order to perform an analysis.

In a specific embodiment, means for drying the sensing element 8 may be provided. The drying means may be operable to dry the sensing element after each exhalation of the subject, for example and preferably during the succeeding inhalation. In one embodiment, the sensing element is disposed so as to be contacted by the gas stream inhaled by the subject. In this way, the relatively low humidity gas stream being inhaled is used to remove moisture from the sensing element. In one simple embodiment, the gas stream to dry the sensing element is provided by an aperture being positioned to direct a stream of air onto the sensing element as the subject inhales.

Alternatively, the sensor assembly may be provided with a supply of pressurized dry or reference gas, a stream of which is directed to impinge upon the sensing element. The flow of pressurized gas may be intermittent with the pressurized gas being supplied only during the periods in which the subject is inhaling. More preferably, the flow of pressurized gas is continuous, thereby providing a constant feed of dry gas to the sensor element. In such a case, the volumetric flow rate of the pressurized gas is sufficiently high to remove water from the sensing element to the required level, while being sufficiently low to not interfere with the response of the sensing element to the changes in content of water vapour in the exhaled gas stream of the subject. The pressurized gas may be any suitable gas, for example air. One preferred gas is oxygen or oxygen-enriched air, which is frequently supplied to a subject to assist with many conditions. In such a case, the sensor assembly may be arranged such that the pressurized gas may be inhaled by the subject. In this arrangement, it is preferred that the supply of pressurized gas is divided into two streams, a first major stream being supplied directly for inhalation by the subject, and a second minor stream directed to the sensing element to perform the drying function. The ratio of flow-rates of the first and second streams may be in the range of from 5:1 to 25:1, more preferably from 10:1 to 20:1.

Alternatively, the means of drying may include (but not necessarily limited to); infrared or microwave radiation.

Figure 5:
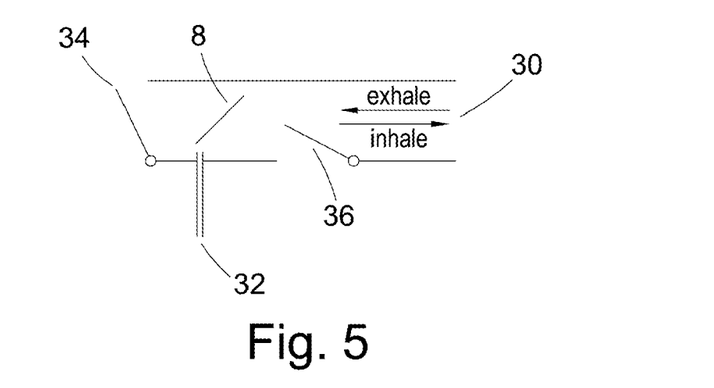

FIG. 5 illustrates a cross section view of a preferred embodiment of the sensor. In this case the sensor has a mouthpiece 30 through which a subject can inhale and exhale. The sensing element 8 is disposed to allow exhaled gas to impinge upon its surface. A conduit 32 is provided though which drying gas can be provided. This may be in the form of a positive pressure of dry reference gas, or may simply be an opening through which air is drawn when the subject inhales. The drying gas is used to dry the sensing element 8 between exhalations. A valve 34 is provided at an end of the sensor opposite to the mouthpiece 30. A further valve 36 is provided disposed between the sensing element 8 and the mouthpiece 30.

When the subject exhales, valve 36 closes and valve 34 opens, allowing the exhaled gas stream to impinge on the sensing element and leave the sensor. When the subject inhales, valve 34 closes preventing air from entering the sensor other than through the conduit 32, and valve 36 partially opens. This ensures that drying gas from the conduit 32 passes over the surface of the sensing element 8 and dries the sensing element 8.

Figure 6:
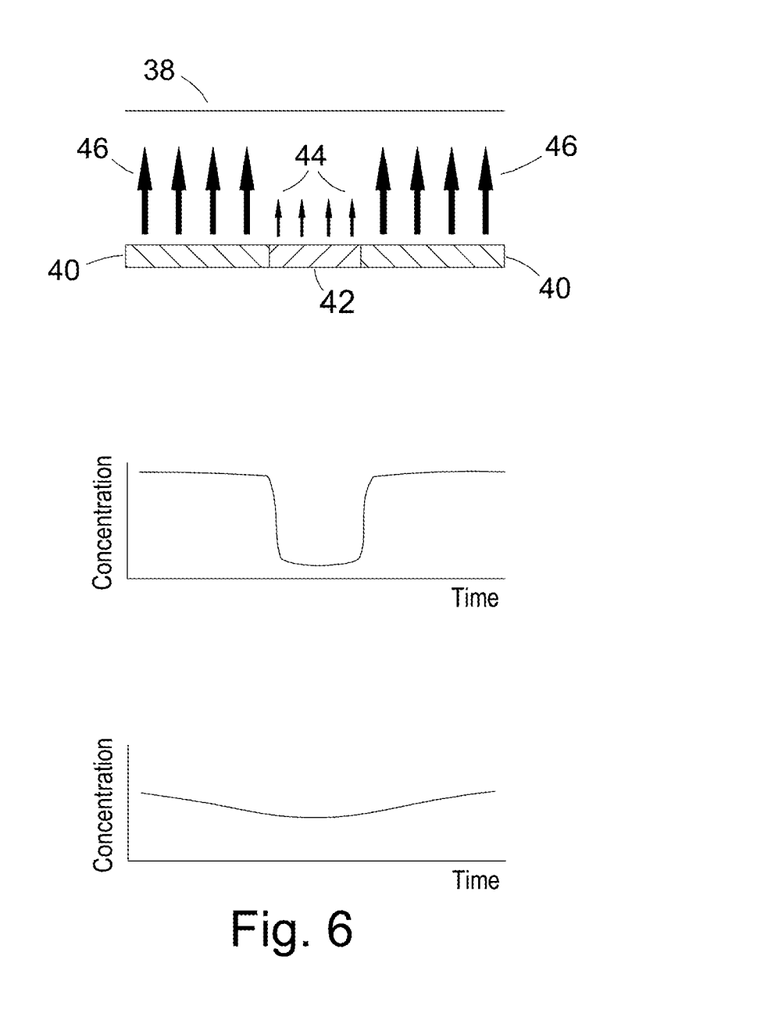

The importance of turbulence in the exhaled gas stream is illustrated in FIG. 6. FIG. 6a is a schematic illustration of water evaporating at differential rates from a surface into a tube 38 such as the inside surface of an airway in a respirator system or the sensing apparatus. The surface permits water to evade the surface but has two difference regions of evasion 40 and 42. Region 42 restricts water to evade the surface at a slow rate 44, whereas region 40 permits water to evade the surface at a much faster rate 46. When exhaling, the atmosphere is "swept" from the tube such that it can later be passed over a sensing element 8 and the water content (or temperature) measured.

FIG. 6b illustrates the case where the atmosphere is swept out of the tube under turbulent conditions (having a Reynolds number>2000). The measurement of water content reveals that there is a clear discontinuity between the three regions with very little mixing. As a space occupying lesion would allow water evaporation at a different rate, such a discontinuity is likely to have arisen from a space occupying lesion.

FIG. 6c illustrates the case where the atmosphere is swept out of the tube under laminar flow conditions (having a Reynolds number<2000). In this case the measurement of the water profile concentration reveals that there is mixing between the three regions, and a discontinuity arising from the presence of a space occupying lesion is much more difficult to detect.

For the reasons described above, it is important for the subject to inhale and exhale at a fast rate to ensure that turbulent conditions are achieved.

Example 1

Humidity profiles were obtained in trial conducted on subjects using an electrochemical sensor prepared as follows:
Sensor Construction A sensor assembly having the general configuration shown in FIG. 3 was prepared. The electrodes were coated with an ion exchange layer comprising a commercially available sulphonated tetrafluoroethylene copolymer (Nafion®, ex Du Pont)

Using this type of sensor device to obtain humidity profiles of water vapour content versus time for exhaled breath a number of subjects were identified who gave profiles with an indent in the phase II initial upward curve portion. The health of these subjects was subsequently further investigated and the indents correlated with a lung lesion.

Example 1a

A subject A known to be suffering from interstitial lung disease was caused to exhale into the sensor assembly. The change in the content of water vapour during the time of the exhalation was determined and the profile is shown in FIG. 7.

The profile follows the general pattern described above, that is having Phases I, II, III and IV bounded by points A, B, C, D and E, as described above and expected of a healthy subject. However, as can be seen from the figure, an irregularity can be identified in the profile in the region indicated as X, corresponding to the middle to later portion of Phase II of the profile. In particular, the profile indicates that the general increase in water vapour content over time during Phase II slowed at point Y. After point Y, the content of water vapour detected in the exhaled gas stream was less than expected. The expected increase in water vapour content, as determined by interpolation between the start and end points of Phase II, is shown by way of the dotted line Z. It can be seen that during the middle to later portion of Phase II, the content of water vapour was lower than that indicated by the line Z.

Figure 7:
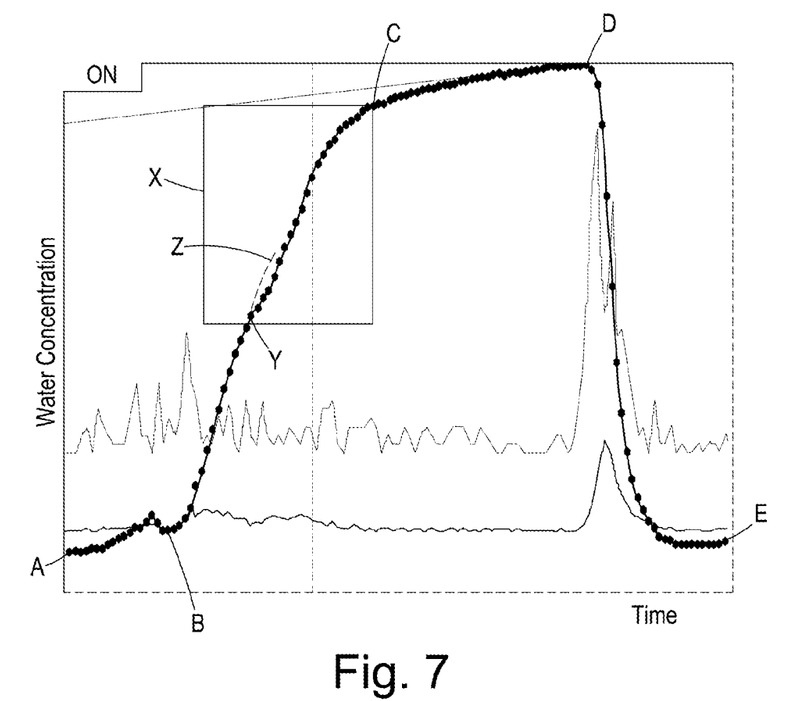

In addition, the gradient of Phase II of the profile of FIG. 7 was lower than expected, indicating that throughout Phase II, the content of water vapour in the exhaled gas stream was less than expected had the subject been healthy. Further, the duration of Phase III of the profile is lower than expected had the subject been healthy.

Example 1b

Subject B, a male, 36 years of age, ex-smoker, was asked to exhale into the sensor assembly. The assembly determined the change in water vapour content over the time of exhalation. The profile thus generated is shown in FIG. 8.

Figure 8:
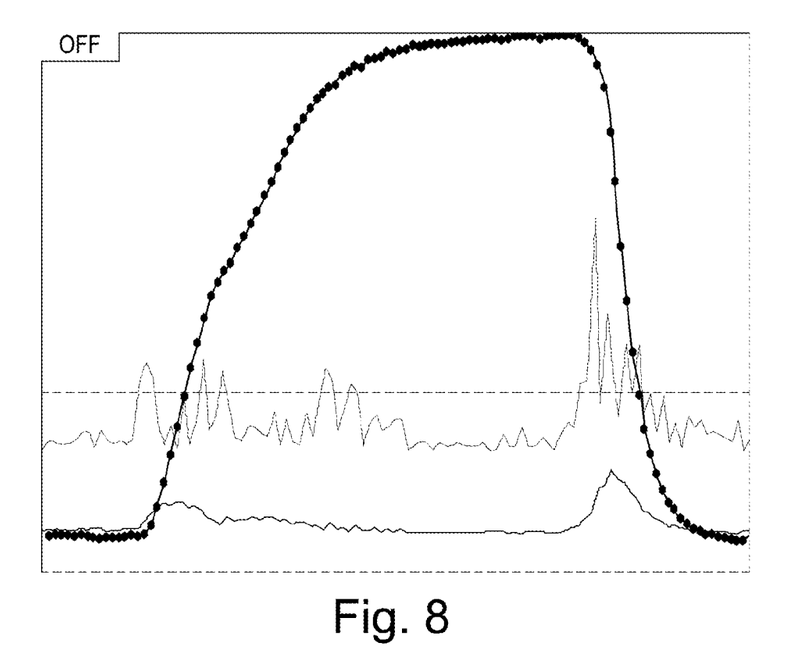

As can be seen, by comparing the profile of FIG. 8 of Subject A with the profile of FIG. 1 of a healthy person, it can be noted that Phase II of the profile contains a deviation from the pattern expected of a healthy subject. In particular, it can be seen that the profile is not smooth and contains a discontinuity, such that the content of water vapour in the gas exhaled during the middle to later portion of Phase II was lower than expected. Subject A was subjected to further investigations.

Subject B complained of chest and back pains, was diagnosed as having dyspnea and a dry cough. Further examination of the subject revealed the right lung to be normal, but the left lung to be compressed at the upper lobe bronchus. A CT scan was conducted and a tumour was identified in the left lung.

Example 1c

Subject C, a male, 70 years of age, ex-smoker, was asked to exhale into the sensor assembly. The assembly determined the change in water vapour content over the time of exhalation.

The profile of water vapour content against time of exhalation of Subject C contained a significant deviation from the pattern expected. In particular, Phase II of the profile was not a smooth curve and contained a discontinuity, such that the content of water vapour in the gas exhaled during the middle to later portion of Phase II was lower than expected. Subject B was subjected to further investigations.

Subject B was diagnosed as having COPD II and dyspnea. Tissue analysis by way of fine needle aspiration cytology (FNAC) indicated the presence of an adenocarcinoma.

Example 1d

Subject D, a male, 60 years of age, ex-smoker, was asked to exhale into the sensor assembly. The assembly determined the change in water vapour content over the time of exhalation.

The profile of water vapour content against time of exhalation of Subject D contained a significant deviation from the pattern expected. In particular, Phase II of the profile was not a smooth curve and contained a discontinuity, such that the content of water vapour in the gas exhaled during the middle to later portion of Phase II was lower than expected. Subject D was subjected to further investigations.

Subject D complained of a cough and chest pains. A CT scan indicated the presence of a sizeable lesion in the left lung of the subject. Tissue analysis by way of fine needle aspiration cytology (FNAC) indicated the presence of an adenocarcinoma.

Example 1e

Subject E, a male, 55 years of age, ex-smoker, was asked to exhale into the sensor assembly. The assembly determined the change in water vapour content over the time of exhalation.

The profile of water vapour content against time of exhalation of Subject E contained a significant deviation from the pattern expected. In particular, Phase II of the profile was not a smooth curve and contained a discontinuity, such that the content of water vapour in the gas exhaled during the middle to later portion of Phase II was lower than expected. Subject E was subjected to further investigations.

Subject E complained of a cough and chest pains. A CT scan and fine needle aspiration cytology (FNAC) confirmed the presence of emphysema and an inflammatory lesion in the subject's left lung. A tissue biopsy indicated the presence of a small cell carcinoma in the left lung of Subject E.

Example 1f

Subject F, a male smoker, was asked to exhale into the sensor assembly. The assembly determined the change in water vapour content over the time of exhalation.

The profile of water vapour content against time of exhalation of Subject F contained a significant deviation from the pattern expected. In particular, Phase II of the profile was not a smooth curve and contained a discontinuity, such that the content of water vapour in the gas exhaled during the middle to later portion of Phase II was lower than expected. Subject E was subjected to further investigations.

Subject F complained of a cough and mild chest pains. CT-guided FNAC and a tissue biopsy confirmed the presence of a squamous cell carcinoma in the middle of the right lung of Subject F.

Example 2

A further trial was carried out with a dual humidity sensor apparatus to determine factors which enhance detection of discontinuities in humidity profiles of exhaled breath indicative of a respiratory system lesion

Example 2a

Subject G, a 50 year old male, 42 kg, heavy smoker, was asked to exhale into the sensor assembly. The assembly determined the change in water vapour content as simultaneously measured by two sensors over the time of exhalation.

The profile of water vapour content against time of exhalation of Subject G contained a significant deviation from the pattern expected. In particular, Phase II of the profile was not a smooth curve and contained a discontinuity, such that the content of water vapour in the gas exhaled during the middle to later portion of Phase II was lower than expected. Subject G was subjected to further clinical investigations.

Subject G presented with a cough, mild anorexia, weight loss with mild chest pains and sounds. Subsequent bronchoscopy and a tissue biopsy confirmed the presence of a mitotic lesion in right principal bronchus of Subject G.

Example 2b

Subject H, a 75 year old male, 45 kg, ex-smoker, was asked to exhale into the sensor assembly. The assembly determined the change in water vapour content as simultaneously measured by two sensors over the time of exhalation.

The profile of water vapour content against time of exhalation of Subject H contained a significant deviation from the pattern expected. In particular, Phase II of the profile was not a smooth curve and contained a discontinuity, such that the content of water vapour in the gas exhaled during the middle to later portion of Phase II was lower than expected. Subject H was subjected to further clinical investigations.

Subject H presented with a mild cough, anorexia, weight loss with mild chest pains, mild dyspnea, no haemoptysis, and no chest sounds. Subsequent CT-guided FNAC tissue biopsy confirmed the presence of an adenocarcinoma in the right middle lung of Subject H.

Example 2c

Subject J, a 51 year old male, 60 kg, ex-smoker, was asked to exhale into the sensor assembly. The assembly determined the change in water vapour content as simultaneously measured by two sensors over the time of exhalation.

The profile of water vapour content against time of exhalation of Subject J contained a significant deviation from the pattern expected. In particular, Phase II of the profile was not a smooth curve and contained a discontinuity, such that the content of water vapour in the gas exhaled during the middle to later portion of Phase II was lower than expected. Subject J was subjected to further clinical investigations.

Subject J presented with a cough, anorexia, mild weight loss, mild chest pains, severe dyspnea, haemoptysis, but no chest sounds. Subsequent bronchoscopy indicated a fleshy 2 cm growth in the right principal bronchus. Subsequent CT imaging confirmed the presence of a small cell carcinoma in the central lung of Subject J.

Example 2d

Subject K, a 65 year old male, 65 kg, smoker, was asked to exhale into the sensor assembly. The assembly determined the change in water vapour content as simultaneously measured by two sensors over the time of exhalation.

The profile of water vapour content against time of exhalation of Subject K contained a significant deviation from the pattern expected. In particular, Phase II of the profile was not a smooth curve and contained a discontinuity, such that the content of water vapour in the gas exhaled during the middle to later portion of Phase II was lower than expected. Subject K was subjected to further clinical investigations.

Subject K presented with a mild cough, mild anorexia, weight loss, mild chest pains, dyspnea, haemoptysis, no chest pain, and abnormal chest sounds. Subsequent bronchoscopy indicated a growth in the right lower lobe bronchus. Subsequent CT-guided FNAC tissue biopsy confirmed the presence of a small cell carcinoma in the middle right lung of Subject K.

Example 2e

Subject L, a 60 year old male, 42 kg, smoker, was asked to exhale into the sensor assembly. The assembly determined the change in water vapour content as simultaneously measured by two sensors over the time of exhalation.

The profile of water vapour content against time of exhalation of Subject L contained a significant deviation from the pattern expected. In particular, Phase II of the profile was not a smooth curve and contained a discontinuity, such that the content of water vapour in the gas exhaled during the middle to later portion of Phase II was lower than expected. Subject L was subjected to further clinical investigations.

Subject L presented with a mild cough, severe anorexia, weight loss, mild chest pains, dyspnea, no haemoptysis, chest pain but no chest sounds. Subsequent x-ray indicated a small opacity in the mid left lung. Subsequent CT-guided FNAC tissue biopsy confirmed the presence of squamous cell carcinoma in the peripheral left lung of Subject L.

In an alternative embodiment, a similar profile may be obtained of the temperature of the exhaled air stream with respect to time. The Péclet number relates mass diffusion to thermal diffusion. The indent in a humidity profile of water content with respect to time that is indicative of a space occupying respiratory system lesion will also appear in a profile of the temperature of the exhaled air stream with respect to time. In order to observe the indent in a plot of temperature with respect to time, a temperature sensor is required for measuring the temperature of the exhaled air stream that is both accurate and has a fast response rate.

Many methods have been developed for measuring temperature. Most of these rely on measuring some physical property of a working material that varies with temperature. For example, a common device for measuring temperature is the glass thermometer; a glass tube filled with mercury or some other liquid, which acts as the working fluid. Temperature increases cause the fluid to expand, so the temperature can be determined by measuring the volume of the fluid.

Care must be taken when measuring temperature to ensure that the measuring sensor is really at the same temperature as the exhaled air stream being measured.

Under some conditions, heat from the measuring instrument can cause a temperature gradient, so the measured temperature is different from the actual temperature of the exhaled air stream. In such a case the measured temperature will vary not only with the temperature of the system, but also with the heat transfer properties of the system. Air velocity increases the rate of heat transfer from the sensor, resulting in a difference in temperature reading for the same ambient temperature. For example, the mass of a glass thermometer is often so large that the indicated temperature significantly lags behind the actual change in temperature. Such sensors need rapid speed of response to measure the profile of the exhaled air stream. These factors need to be considered when selecting a sensor for measuring the temperature profile.

There are several devices for measuring temperature that may be suitable in this application. These include thermocouples, thermistors, a Resistance Temperature Detector (RTD), pyrometers, infrared spectroscopy, Langmuir probes (for electron temperature of a plasma), changes in the speed of sound and other types of thermometers such as bimetallic strips, gas thermometer, vapour-tension, etc.

A preferred embodiment is to measure absorbance loss of an infrared light beam shone through a gas flow cell (with appropriate transparent end windows) positioned across the flow of the exhaled air stream. It will be appreciated that this embodiment is otherwise compatible with the embodiment that uses a humidity sensor.

It will be appreciated by the person of skill in the art that various modifications may be made to the above-described embodiments without departing from the scope of the present invention.

The invention claimed is:

1. A method of preselecting a test subject for determination of the presence of a space-occupying respiratory system lesion, said method comprising:
   determining a humidity profile of exhaled air of said test subject by measuring change of water vapour content after the start of exhalation of said test subject;
   comparing, using a processor, a water vapour content of the test subject at a time point after the start of exhalation with a control water vapour content in an exhalation of a person who does not have a respiratory system lesion measured at the same time point after the start of exhalation; and
   determining, using said processor, whether said humidity profile of exhaled air of said test subject exhibits an irregularity indicative of such a lesion based on said comparison, wherein said irregularity equates to a lower water vapour content in exhaled air of said test subject as compared to the control water vapour content at the same time point after the start of exhalation.

2. A method as claimed in claim 1, wherein the method is used for pre-selecting a test subject for further investigation of any of lung cancer, tuberculosis and lung pathology.

3. A method as claimed in claim 1, wherein said humidity profile is obtained using a humidity sensor for sensing water vapour in exhaled air, the sensor comprising:
   a sensing element disposed to be exposed to the exhaled air, the sensing element comprising a working electrode, a counter electrode and a layer of ion exchange material extending between the working electrode and the counter electrode, wherein the ion exchange layer is configured to form an electrical contact between the working and counter electrodes when exposed to water vapour in the exhaled air; and
   wherein said sensor is configured to generate an output representative of the change in concentration of water vapour over time in the exhaled air which is received by said processor.

4. A method as claimed in claim 3 wherein said sensor further comprises:
   a conduit through which the exhaled air is channelled to impinge upon said sensing element, the conduit being arranged to allow turbulent flow in the air stream.

5. A method as claimed in claim 4, wherein the conduit has a bore diameter in a range selected from any of between 10 and 20 mm and between 15 and 18 mm.

6. A method as claimed in to claim 3, wherein the ion exchange material comprises a sulphonated tetrafluomethylene copolymer.

7. A method as claimed in claim 3 wherein the sensor comprises means for drying the sensing element.

8. A method as claimed in claim 7, wherein the means for drying the sensing element comprises any of a side hole adjacent to the sensing element such that during inhalation dry air is passed over the sensing element, a source of infrared radiation, a source of microwave radiation and a source of a dry reference gas.

* * * * *